United States Patent
Chen et al.

(10) Patent No.: US 6,660,265 B1
(45) Date of Patent: Dec. 9, 2003

(54) FRESH, CRYOPRESERVED, OR MINIMALLY CARDIAC VALVULAR XENOGRAFTS

(75) Inventors: Raymond H. Chen, Boston, MA (US); David H. Adams, Boston, MA (US)

(73) Assignee: The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/688,492

(22) Filed: Oct. 16, 2000

Related U.S. Application Data

(60) Provisional application No. 60/159,833, filed on Oct. 15, 1999.

(51) Int. Cl.$^7$ .......................... A01N 63/00; A01N 1/00; C12N 5/00
(52) U.S. Cl. .................. 424/93.7; 435/395; 435/1.1
(58) Field of Search .................. 424/93.7; 435/395, 435/1.1

(56) References Cited

U.S. PATENT DOCUMENTS

| | | |
|---|---|---|
| 5,160,313 A | 11/1992 | Carpenter et al. |
| 5,336,616 A * | 8/1994 | Livesey et al. |
| 5,863,296 A | 1/1999 | Orton |
| 5,882,850 A | 3/1999 | Khor et al. |

FOREIGN PATENT DOCUMENTS

| | | |
|---|---|---|
| EP | 2 143 306 A | 2/1985 |
| WO | WO 95/11047 A1 | 4/1995 |
| WO | WO 99/37337 A2 | 7/1999 |
| WO | WO 00/25705 A1 | 5/2000 |
| WO | WO 01/28604 A1 | 4/2001 |

OTHER PUBLICATIONS

Gonzalez–Lavin et al. (Heart and Vessels, (1987) 3/4 (205–208, see abstract).*
St. Louis et al. (European Journal of Cardio–Thoracic Surgery, (1991) 5 (9) 458–64; discussion 465, see abstract).*
Lim (International Journal of Angiology, (1998) 7/1 (6–9) Refs: 15, see abstract).*
Suh et al. (Yonsei Medical Journal (1999), 40(2), 184–190, see abstract).*
Adams, et al., "Cardiac Xenotransplantation: Clinical Experience and Future Direction", Soc. of Thorac Surg., 2000: 70:320–6, Pub by Elsevier Science Inc.
Adams, et al., "Technique for Heterotopic Pig Heart Xenotransplantation in Primates", Soc. Of Thoracic Surg., 1999: 68:p. 265–8, Pub by Elsevier Science Inc.
Bach, et al., "Delayed xenograft rejection", Immunol Today, Aug. 1996, vol. 17:379–84.
Chen, et al., "Fresh Porcine Cardiac Valves Are Not Rejected In Primates", J of Thorac. & Card. Surg., vol. 119:p1216–1220, Jun. 2000.

Chen, et al., "Hypracute Vascular Rejection Lessons from Pig–to–Primate Xenotransplantation", Vascular Disease and Injury: Preclinical Research. p. 231–43, Totowa: Humana in press, 2000.
Chen et al., "Differential galactose $\alpha(1,3)$ galactose expression by porcine cardiac vascular endothelium", Xenotransplantation, 1999, 6:169–172.
Galili, et al., "Evolutionary relationship between the natural anti–Gal antibody and the Gala3→3Gal epitope in primates", Proc Natl. Acad. Sci. USA, 84:pp. 1369–1373 03/97 pub. Francisco, CA.
Hamilton, et al., "Mitral valve replacement in dogs using pig aortic valve heterografts", Thorax, 1968, 23:pp. 239–248.
Iben, et al. "The histologic and hemodynamic evaluation of viable heterograft valves", Journal of Thor. and Card. Surg., Apr. 1971, vol. 61 No. 4: pp. 556–60.
McGiffin, et al., "Long–Term Results of the Viable Cryopreserved Allograft Aortic Valve: Continuing Evidence for Superior Valve Durability", Journal of Card. Surg. 3:289–296, Supplement 1988.
O'Brien, et al., "The Viable Cryopreserved Allograft Aortic Valve", Journal of Card. Surg., vol. 1, No. 3, 1987, Supplement 1987, pp. 153–167.
O'Brien, et al., "Allograft Aortic Valve Replacement: Long-Term Follow–up", Soc. of Thorac. Surg., 1995, 60:S65–70.
O'Brien, et al., "Allograft Aortic Valve Replacement: Long-Term Comparative Clinical Analysis of the Viable Cryopreserved and Antibiotic 4° C Stored Valves", Journal of Card. Surg. Dec. 1991, vol. 6 No. 4, Supplement p. 534–43.
O'Brien, et al., "A comparison of aortic valve replacement with viable cryopreserved and fresh allograft valves, with a note on chromosomal studies", J. Thorac Card. Surg. 1987;94:812–23.
O'Brien, et al., "Heterograft aortic valves for human use", J. Thorac. Card Surg. vol. 53, No. 3, p. 392–7 Mar. 1967.
Paneth, et al., "Transplantation of human homograft aortic valve", Thorax (1966), 21, p. 115–7.
Platt et al., "Review Article Acute Vascular Rejection", Xenotransplantation 1998:169–175.
Schoen et al., "Calcification of Bovine Pericardium Used in Cardiac Valve Bioprostheses", Am. J. Pathol 1986, 123:134–45.
Tomazic et al., "Physicochemical properties of calcific deposits isolated from porcine bioprosthetic heart valves removed from patients following 2–13 years function", Journal of Biomedical Materials Research, vol. 28, 35–47, 1994.

\* cited by examiner

*Primary Examiner*—Christopher R. Tate
*Assistant Examiner*—Randall Winston
(74) *Attorney, Agent, or Firm*—Wolf, Greenfield & Sacks, P.C.

(57) ABSTRACT

The invention relates to the preparation of porcine cardiac valve leaflets for implantation into patients.

1 Claim, 1 Drawing Sheet

FRESH, CRYOPRESERVED, OR MINIMALLY CARDIAC VALVULAR XENOGRAFTS

RELATED APPLICATIONS

This application claims priority under 35 U.S.C. §119 to U.S. Provisional Patent Application No. 60/159,833, filed Oct. 15, 1999, the entire contents of which is hereby incorporated by reference.

GOVERNMENT SUPPORT

This invention was made in part with government support under grant No. 1F32HL0996601 from the National Institutes of Health (NIH). The government may have certain rights in this invention.

FIELD OF THE INVENTION

The invention relates to the preparation of porcine cardiac valve leaflets for implantation into patients.

BACKGROUND OF THE INVENTION

Diseased cardiac valves can be replaced with either mechanical or biological tissue prostheses. Mechanical valves are more durable but require long-term anticoagulation therapy with coumadin to prevent surface clotting. Risks associated with anticoagulation therapy, such as bleeding or thromboembolism, are of concern to many physicians and their patients. Biological tissue valves as prostheses, on the other hand, do not require anticoagulation therapy.

Xenografts are a desirable source of biological tissue, but xenotransplantation is currently performed using highly preserved tissues to avoid rejection. The presentation techniques eliminate tissue viability and may result in post-implant calcification that shortens the half-life of the implant. Therefore, the usefulness of preserved implants is limited by durability secondary to structural degeneration and/or calcification.

The first reported use of formaldehyde on valves was to denature and stiffen elastic fibers in human homografts (Paneth et al, Thorax, 21:115–7. 1966). Initial formaldehyde preservation of porcine valves was performed by O'Brien, who used the solution in 1967 for "both preservation and sterilization" (O'Brien, J. Thoracic Cardiovasc. Surgery, 53:392–7. 1967). Early investigators hypothesized that the fixative denatured the proteins of the graft, thereby minimizing rejection. (See: Hamilton et al, Thorax, 23:239–48. 1968; Paneth et al, Thorax, 21:115–7. 1966). Currently, biological tissue valves are constructed with glutaraldehyde-fixed porcine or bovine tissues, which may explain the considerably reduced biological half-life of these xenotransplanted valves as compared to native human valves.

The transplantation of porcine hearts into humans prompts a violent hyperacute rejection similar to that seen in ABO-incompatible transplantation, in which the graft becomes cyanotic, and edematous minutes after implantation (Chen et al, In: Simon D, Roberts C, eds. Vascular Disease and Injury: Preclinical Research. Ottowa: Humana, in press, 2000). The extensive microvascular thrombosis of hyperacute rejection is the result of IgM-triggered, complement Membrane Attack Complex (MAC)-mediated graft destruction. This mechanism of pig-to-human xenotransplantation rejection was not understood until 1987, when it was shown that humans constituitively synthesize natural IgM antibodies against a porcine molecule, galactose α-1,3 galactose (Galili et al, Proc Natl Acad Sci USA, 84:1369–73. 1987).

In contrast, is the novel and unexpected finding that isolated porcine cardiac valve leaflets lack galactose-α 1,3-galactose expression and are therefore non-immunogenic in humans and other primates. This surprising finding is the basis for preparing porcine cardiac valve leaflets with little or no contact with fixative agents. These unfixed and minimally fixed tissues can be successfully used as xenografts. According to the invention, because these isolated porcine cardiac valve leaflet tissues show no immunogenicity in the host, they can be used either untreated or minimally treated with fixatives, thereby increasing implant viability and durability over that of past implants, and overcoming some of the limitations of xenotransplantation.

SUMMARY OF THE INVENTION

The invention is based on the surprising finding that porcine cardiac valve leaflets do not express galactose-α 1,3-galactose and are not immunogenic when implanted into primates. Accordingly, the invention is related to preparations of isolated porcine cardiac valve leaflets for implantation into patients. The invention also relates to methods for preserving isolated porcine cardiac valve leaflets prior to implantation into patients, such as fixation-free, minimal fixed, and/or cryopreserved. In addition, the invention relates to methods of treating a patient by implantation into the patient of a fixation-free, minimal-fixed and/or cryopreserved porcine cardiac valve leaflet or leaflets.

In one aspect of the invention a medical preparation is provided. The preparation contains an isolated porcine cardiac valve leaflet, free of contact with an exogenous fixative. In one embodiment the preparation is packaged sterile in a container in an extracellular solution. In another embodiment, the extracellular solution contains a cryoprotectant agent. In another embodiment, the preparation is frozen.

Another aspect of the invention provides a kit for implanting a cardiac valve leaflet into a patient. The kit is a container including an isolated porcine cardiac valve leaflet, free of contact with a fixative, packaged sterile in a container in an extracellular solution. The kit also contains written instructions for processing the isolated porcine cardiac valve leaflet for implantation into a patient. In one embodiment of the kit, the extracellular solution contains a cryoprotectant. In other embodiments, the leaflet is frozen.

Yet another aspect of the invention provides a medical preparation. The preparation is an isolated porcine cardiac valve leaflet, contacted for a time with an amount of an exogenous fixative effective to prolong shelf-life versus an uncontacted porcine cardiac valve leaflet, but wherein said time and amount are insufficient to induce a calcification level of a percentage which is more than 80% of an identical-interval, post-implantation calcification level of a porcine cardiac valve leaflet contacted 6 hours with 0.65% gluteraldehyde. The preparation can be packaged sterile in a container in an extracellular solution. A preferred percentage of calcification is less than 80%, 70%, 60%, 50%, 40%, 30%, 20%, 15%, 10%, 5%, 2%, or 1%, of the level of calcification characteristic of an identical-interval, post-implantation calcification level of a porcine cardiac valve leaflet contacted 6 hours with 0.65% gluteraldehyde and implanted. In one embodiment, the contact with the fixative is for equal to or less than 120, 60, 30, 25, 20, 15, 10, 5, 4, 3, 2, 1, 0.5 minutes. In one embodiment, the fixative is gluteraldehyde. In another embodiment, the fixative is gluteraldehyde and contacts the preparation for 2 hours or less. In another embodiment, the fixative is 0.60%, 0.55%, 0.45%, 0.35%, 0.25%, 0.15%, 0.10%, 0.05%, 0.01% or 0.001% gluteraldehyde. In another embodiment, the fixative is ethanol. In another embodiment, the fixative is ethanol and contacts the preparation for 1 hour or less. In yet another embodiment, the fixative is acetone. In another embodiment, the fixative is acetone and contacts the preparation for 1 hour or less. In another embodiment, the extracellular solution contains a cryoprotectant agent. In another embodiment, the preparation is frozen.

Another aspect of the invention provides a cryopreserved implant that is a frozen isolated porcine cardiac valve leaflet with a predicted shelf-life of 13 months or more and a predicted post-implantation half life of 13 years or more when thawed and implanted into a patient. In one embodiment, the predicted post-implantation half life of the implant is determined by the level of leaflet calcification post implantation. In another embodiment, the predicted level of implanted valve leaflet calcification level is less than 80% of the identical-interval post-implantation calcification level of a porcine cardiac valve leaflet contacted 6 hours with 0.65% gluteraldehyde. The leaflet can be packaged sterile in a container. The range of calcification level, the range of times of exposure, and preferred fixatives and fixative solutions are as described above herein.

Another aspect of the invention provides a kit for implanting a cardiac valve leaflet into a patient. The kit is a container including an isolated porcine cardiac valve leaflet, contacted for a time with an amount of an exogenous fixative effective to prolong shelf-life versus an uncontacted porcine cardiac valve leaflet, but wherein said time and amount are insufficient to induce a percentage of calcification level of 80% of the identical-interval, post-implantation calcification level of a porcine cardiac valve leaflet contacted 6 hours with 0.65% gluteraldehyde; packaged sterile in a container in an extracellular solution. A preferred range of calcification level, the range of times of exposure to fixative, and preferred fixatives and fixative solutions are as described above herein. The kit also contains written instructions for processing the isolated porcine cardiac valve leaflet for implantation into a patient. In one embodiment, the extracellular solution contains a cryoprotectant agent. In another embodiment, the preparation is frozen.

Another aspect of the invention is a method of preparing an isolated porcine cardiac valve leaflet for implantation into a patient. In the method, an isolated porcine cardiac valve leaflet is contacted for a time with an amount of an exogenous fixative effective to prolong shelf-life versus an uncontacted porcine cardiac valve leaflet, but wherein said time and amount are insufficient to induce a percentage of calcification level of 80% of the identical-interval, post-implantation calcification level of a porcine cardiac valve leaflet contacted 6 hours with 0.65% gluteraldehyde, and the contacted isolated leaflet is packaged sterile in a container in an extracellular solution. A preferred range of calcification level, range of times of exposure to fixative, and preferred fixatives and fixative solutions are as described above herein. In one embodiment, the extracellular solution contains a cryoprotectant agent. In yet another embodiment, the isolated porcine cardiac valve leaflet is frozen.

Another aspect of the invention is a method of preparing an isolated porcine cardiac valve leaflet for implantation in a patient. In the method, the isolated porcine cardiac valve leaflet is processed for implantation without contact with an exogenous fixative. The leaflet can be held or packaged fresh, sterile in a container in an extracellular solution. In another embodiment, the extracellular solution contains a cryoprotectant agent. In yet another embodiment, the isolated porcine cardiac valve leaflet is frozen.

Another aspect of the invention is a method of treating a patient that is implanting into the patient one or more isolated porcine cardiac valve leaflets which have been contacted for a time with an amount of an exogenous fixative, wherein said time and amount are insufficient to induce a percentage of calcification level of 80% of the identical-interval, post-implantation calcification level of a porcine cardiac valve leaflet contacted 6 hours with 0.65% gluteraldehyde. A preferred range of calcification level, range of times of exposure to fixative, and preferred fixatives and fixative solutions are as described above herein. In one embodiment, the leaflet has not previously been frozen. The leaflet may be obtained fresh, i.e., recently harvested without overnight storage. In another embodiment, the method involves thawing a leaflet, the leaflet having been stored frozen.

Another aspect of the invention is a method of treating a patient that is thawing and implanting into the patient one or more isolated porcine cardiac valve leaflets which have been contacted for a time with an amount of an exogenous fixative, wherein said time and amount are insufficient to induce a percentage of calcification level of less than 80% of the identical-interval, post-implantation calcification level of a porcine cardiac valve leaflet contacted 6 hours with 0.65% gluteraldehyde. A preferred range of calcification level, range of times of exposure to fixative, and preferred fixatives and fixative solutions are as described above herein.

Another aspect of the invention is a method of treating a patient that is implanting one or more isolated porcine cardiac valve leaflets which have been prepared for implantation without contact with an exogenous fixative. The method can involve obtaining a leaflet that may be fresh, i.e., recently harvested without overnight storage. The leaflet also may have been stored in a non fixative storage solution. In one embodiment, the leaflet is stored at bout 4° centigrade. In another embodiment, the method involves thawing the leaflet, the leaflet having been stored frozen.

For any of the forgoing embodiments, an exogenous fixative includes any tissue fixative agent or means, known to those of ordinary skill in the art. Thus, an exogenous fixative preferably is one selected from the group consisting of chemical or irradiation fixatives.

DETAILED DESCRIPTION OF THE INVENTION

Figure 1:
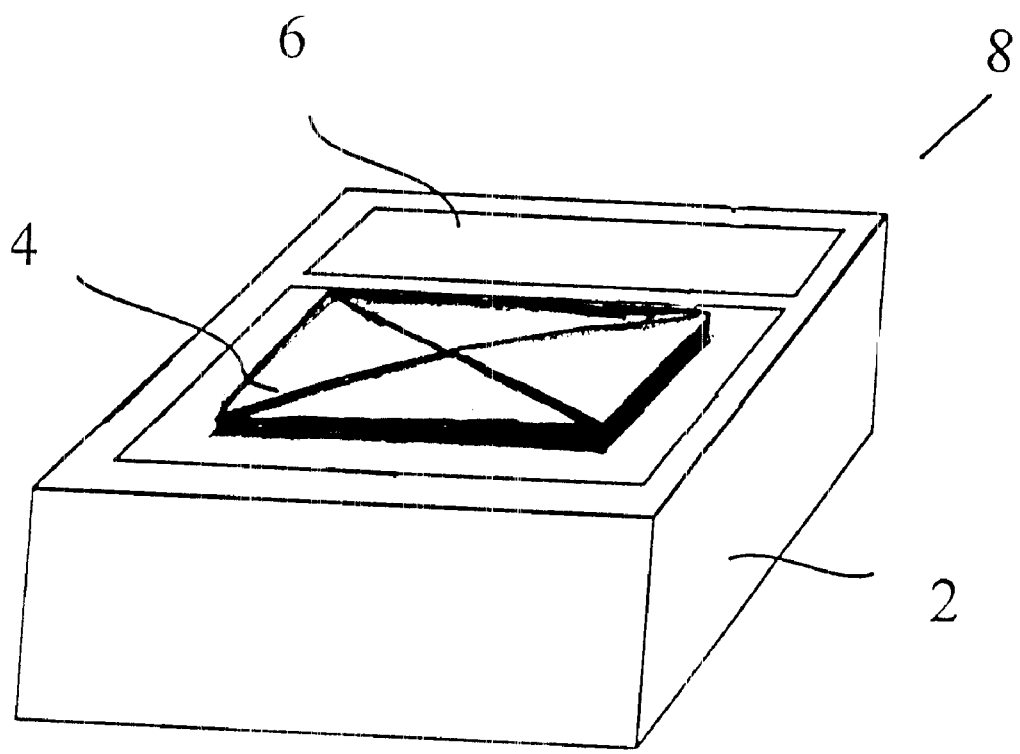
FIG. 1 is a diagram of a kit according to the invention.

The invention is based on the surprising finding that porcine cardiac valve leaflets lack galactose-α 1,3-galactose expression and are non-immunogenic when implanted into primates. Accordingly, the invention is related to preparations of isolated porcine cardiac valve leaflets for implantation into patients. The invention also relates to methods for preserving isolated porcine cardiac valve leaflets prior to implantation into patients, such as fixation-free, minimal fixed, and/or cryopreserved. In addition, the invention relates to methods of treating a patient by implantation of a fixation-free, minimal-fixed and/or cryopreserved porcine cardiac valve leaflet or leaflets.

As used herein, an "isolated" porcine cardiac valve leaflet is a leaflet separated from other porcine cardiac valve tissue, which has been removed from the donor using standard surgical methods. (See: Iben et al, The Journal of Thoracic and Cardiovascular Surgery, 61(4): 556–560. 1971; Chen et al., The Journal of Thoracic and Cardiovascular Surgery, 119(6):1216–1220. 2000). In essence, the valve leaflet is separated from tissue that would induce an immune response when implanted into a patient, i.e., tissue expressing galactose-α 1,3-galactose.

The isolated cardiac valve leaflet may be prepared for implantation without any contact with exogenous fixatives, including mechanical preservatives. There are numerous fixatives known in the art, including but not limited to: chemical fixative agents such as formalin, gluteraldehyde, acetone, ethanol, acrolein; or other fixative agents such as irradiation/UV light exposure. In the invention, the preferred exogenous fixatives include, but are not limited to: gluteraldehyde, acetone, and ethanol. The term "free of contact with a fixative" means the isolated porcine cardiac valve is not touched or been exposed to any exogenous fixative before or after isolation from all other porcine cardiac tissue, and prior to sterile packaging, freezing, and/or implantation into a patient. A valve leaflet prepared for implantation in this manner will not induce a significant immune response, as described in the examples below, even though the leaflet has not been treated with fixatives used in the prior art to reduce the immunogenicity of the implanted tissue. Thus, the leaflet is free of characteristics, including surface characteristics such as cross-linking, dead cell levels, and post-implantation properties of a leaflet treated with an exogenous fixative according to prior-art methods.

In other embodiments, the isolated cardiac valve leaflet may be contacted with an exogenous fixative but in an amount and/or for a time and/or temperature so as to produce substantially less surface alteration (e.g. surface crosslinking) than is characteristic of that alteration resulting from fixative agents used in the methods of the prior art. The exposure to fixative agents as described herein increases durability of the implant, but exposure is in an insufficient amount as would be necessary to render tissue expressing galactose-α 1,3-galactose non-immunogenic (which, surprisingly, is not needed for isolated valve leaflets). As described in greater detail below, conditions including fixative agents are applied to increase durability and integrity of the implanted tissue, lessening the calcification-inducing effects of such fixative agents when applied at levels characteristic of the prior art. The percentage of fixative may range from less than .01% to 100% of the fixative in solution. Thus, the percentage of fixative can .01, .02, .03, .04, .05, .06, .07, .08, .09, .10, .15, .2, .25, .3, .35, 0.4, .45, .5, .55, .6, .65, .7, .75, .8, .85, .9, .95, 1, 2, 3, 4, 5, 6, 7, 8, 9, 10, 11, 12, 13, 14, 15, 16, 17, 18, 19, 20, 21, 22, 23, 24, 25 percent, and so on, up to 100% embracing every integer therebetween.

As used herein, the term "contacted with" exogenous fixative agent means the porcine cardiac valve leaflet, before or after isolation from all other porcine cardiac tissues, and prior to sterile packaging, freezing and/or implantation, is placed into contact with an exogenous fixative. Examples of such contact include, but are not limited to, immersion of the porcine cardiac tissue in the exogenous fixative, rinsing the porcine cardiac tissue with the exogenous fixative, or perfusion, etc. In some embodiments, the length of immersion may range from less than one minute to up to and including two hours or more. Contact may also include contact with radiation such as UV light.

The isolated cardiac valve leaflet may be sterilized with methods known to those of skill in the art, including, but not limited to irradiation (e.g. Y-irradiation) and antibiotic treatment. Antibiotic treatments may include, but are not limited to, contact of the porcine cardiac valve leaflet with amphotericin B, polymixin B sulfate, cefoxitin, vancomycin, lincomycin and/or other antibiotics, all of which are known in the art (see U.S. Pat. No. 4,890,457). Sterilization may occur before or after isolation of the porcine cardiac valve leaflet from all other porcine cardiac tissues.

The isolated cardiac valve leaflet may be packaged with an extracellular solution in a sterile container, which may include, but is not limited to: a sterile bag, box, or jar. Packaging may be for long-term storage, or for short transport, for example for delivery of fresh, unfixed leaflets from a donor to a recipient in a surgical suite. As used herein, "extracellular solution" may be saline, culture media, cardioplegia, or any other tissue-preservation or storage solutions, all of which are well known to those of skill in the tissue transplantation art. In all embodiments the extracellular solution will be sterile. In preferred embodiments, the extracellular solution is a non-fixative solution containing only non-fixative agents, i.e., does not contain an exogenous fixative.

The isolated porcine cardiac valve leaflet may be superficially wetted with the extracellular solution, (i.e. the solution remaining after gravity-induced dripping or shaking of the leaflet), or may be contained in a sufficient volume of extracellular solution to submerge the isolated porcine cardiac valve leaflet. In some embodiments the volume may be about, but is not limited to: 5 ml, 10 ml, 25 ml, or 50 ml of extracellular solution.

In some embodiments of the invention, the extracellular solution may contain a cryoprotectant. There are numerous cryoprotectant agents known in the art including but not limited to: dimethylsulfoxide (DMSO), glycerol, albumin, mono- and dissaccharides, and serum (e.g. fetal calf serum, eagle serum, etc). In the invention, the preferred cryoprotectant agents include, but are not limited to: dimethoysulfoxide (DMSO), glycerol, or albumin. Cryoprotectants are routinely used in the art to prevent tissue damage during freezing. In the invention, the percentage of cryoprotectant in the extracellular solution may lie in a range of percentages and the cryoprotectants may be used alone or in combination. For example, the percentage of DMSO may range from 0% to 25%, the percentage of glycerol may range from 0% to 25% and the percentage of albumin may range from 0% to 50%. The components and percentage of cryoprotectant in the extracellular solution may be determined by one of ordinary skill in the art. The components and amounts used are according to art-accepted methods.

Another element of the invention is a medical preparation of an isolated porcine cardiac valve leaflet with an expected "pre-implantation shelf-life" of 13 months or more and an expected post-implantation half life of 13 years of more. This can be achieved either by freezing, by minimal fixation, or both. Aspects of the invention permit an extension in the pre-implantation shelf-life as well as the post-implantation half-life. The expected pre-implantation shelf-life is the length of time an isolated leaflet may be stored as living tissue after isolating from the donor pig and prior to implantation into a patient.

The isolated leaflets can be used fresh, i.e., within minutes to hours of harvesting from a donor. When used fresh, viability is maximized when compared to leaflets stored overnight or frozen. If a longer shelf-life is desired for commercial and/or practical purposes, then the isolated leaflets can be stored cold or frozen. Freezing, as described in greater detail below, can extend significantly shelf-life, although the freezing conditions and storage time affects post-implantation characteristics such as durability. Thus, there is a trade-off between trying to extend shelf-life and trying to maximize post-implantation desirable characteristics of the isolated leaflets. A surprising discovery, according to the invention, is that better than adequate viability and post-implantation characteristics can be obtained if fresh leaflets are then frozen, stored, thawed and implanted, particularly when this is carried out under the conditions described herein.

A measure of leaflet viability may be the assessment of glucose metabolism in the isolated leaflet to ascertain whether a tissue is living or not. (see O'Brien, M. F. et al, J. Cardiac Surg. 2(Supp):153–167. 1987). Measures of leaflet integrity may also include evaluation of the leaflets for physical or structural tissue breakdown or damage. Alternative methods to assess elements of tissue integrity for implantation are known to those of skill in the tissue transplantation art.

In some embodiments, the porcine cardiac valve leaflet may be not frozen and in other embodiments, the porcine cardiac valve leaflet may be frozen. If frozen, the isolated porcine cardiac valve leaflet may frozen at a temperature within a range including but not limited to: $-20°$ C., $-80°$ C., $-100°$ C., or $-200°$ C. The methodology of cryopreservation is according to art-accepted methods. In some embodiments, the porcine cardiac valve leaflet is frozen in liquid nitrogen.

Freezing unfixed leaflets can extend the shelf-life beyond that of unfixed, unfrozen leaflets, but extremely low temperature freezing such as $-100°$ C. to $-200°$ C. may reduce viability. The use of fresh and unfixed frozen tissues may extend the viability of the cardiac valve leaflets, especially when tissues are frozen at high temperatures (e.g., $0°$ C., $-10°$ C., $-15°$ C., $-20°$ C., $-50°$ C.). Where unfixed tissues (frozen or fresh) may have viability, the use of mild fixation may provide longer shelf-life and perhaps better post-implantation half-life. The tradeoff between the two methods lies in the link between the length of shelf-life and the loss of viability, and both are factors that must be weighed against each other to determine the method of choice.

The isolated leaflets also can be treated with a fixative. The leaflets can be fresh, so treated and immediately transplanted or can be fresh, so treated and stored for transplantation. It is further possible to freeze the isolated leaflets and later, upon thawing, apply fixative, although this is not preferred.

According to the invention, leaflets are "minimally" treated with fixative, as described herein In the prior art, it is common to used fixative to render tissue non-immunogenic. It was discovered, surprisingly, that isolated leaflets do not express galactose-α 1,3-galactose and do not require fixative treatment according to the prior art to avoid immunogenicity. Mild fixative treatment can affect favorably post-implantation characteristics, versus prior-art treatments. Likewise, mild fixative treatment can favorably affect shelf-life (although mild treatment also renders cells nonviable and shelf-life and post-implantation characteristics then are influenced by factors other than viability).

A particularly important feature of mild fixation is the substantially reduced calcification characteristic of prior-art fixed leaflets. The invention also relates to preservation of post-implantation integrity and durability of an isolated porcine cardiac valve leaflet. Determination of post-implantation integrity and durability may be based on the amount of calcification in the implant tissue at various post-implantation time points. Calcification is the presence of mineral and/or calcific deposits in the implanted tissue, which may significantly reduce post-implantation durability of tissues (see: Tomazic, B. B. et al, J. Biomedical Materials Research, Vol. 28: 35–47. 1994). It has been discovered, surprisingly, that calcification levels in isolated valve leaflets can be significantly reduced by avoiding the conditions of fixative agents employed according to the prior art. Because such high levels of fixation can be avoided while still achieving a non-immunogenic implant; implants of higher integrity and durability can be obtained. Calcification levels in implanted porcine valves may begin within days of the implant and increase over time in exogenous-fixative-contacted tissues. For example, at one-year-post implantation, the level of calcification in an implanted porcine cardiac valve leaflet may be significantly higher than calcification levels in the same porcine cardiac valve leaflet at six months post implantation.

Levels of cardiac valve leaflet calcification may be assessed using standard measurement procedures including, but not limited to: chemical analysis, X-ray diffraction, spectroscopy, scanning electron microscopy, polarized light microscopy, and solubility measurement. (see Schoen, et al., American Journal of Pathology, Vol 123, 134–145. 1986). The average statistical level of post-implantation calcification in a stringently fixed cardiac valve leaflet, (for example, leaflets contacted 6 hours with 0.65% gluteraldehyde), may be compared with that in a post-implantation levels in a minimally fixed (as described herein) porcine cardiac valve leaflet. In other embodiments, the level of calcification may be assessed by comparing the level of calcification of the porcine cardiac valve leaflets at the time of implantation with the calcification levels at various times post-transplantation, such as 1, 2, 3, 4, 5, 6, 7, 8, 9, 10, 11, 12, 15, 24, 36, 48, 60, 72, 84, 96, 108, 120 months or more, thereby providing measurement of calcification of an implanted porcine cardiac valve leaflet over time. Thus, the number of months can range from 1 through 120 embracing every integer therebetween.

In other embodiments, levels of calcification in unfixed and minimally fixed tissues may be compared to calcification levels in implanted leaflet tissues that were subjected to stringent fixation methods prior to implantation, as described herein. For example, the 12-month post-implantation level of calcification in a porcine cardiac valve leaflet fixed 5 minutes in 0.05% gluteraldehyde prior to implantation may be compared with the 12-month post-implantation level of calcification in a porcine cardiac valve leaflet fixed 6 hrs in 0.65% gluteraldehyde; providing a comparative measure of calcification resulting from a minimal fixation strategy versus the more stringent fixation strategy.

One aspect of the invention relates to combinations of fixation concentration, fixation time, and fixation temperature to enhance integrity and durability of the implanted cardiac valve leaflet. For example, the fixative may be gluteraldehyde at a concentration between and including 0.001% and 0.6% and the time of contact between the fixative and the isolated porcine cardiac valve leaflets may be between and including 0.01 minute and 120 minutes. In one embodiment the fixative type, concentration, and fixation time results in the post implant calcification levels of less than 60% of the calcification level at the same post-implantation interval in an implanted porcine cardiac valve leaflet treated with 0.65% gluteraldehyde for 6 hours or more prior to implantation. For example, at the same post-implantation interval an isolated porcine cardiac valve contacted 2 minutes in 0.02% gluteraldehyde and implanted will result in less than 60% of the calcification in an isolated porcine cardiac valve contacted 6 hours in 0.65% gluteraldehyde and implanted.

As will be obvious to one of skill in the art, in some embodiments, an isolated porcine cardiac valve leaflet may be contacted with a higher concentration of gluteraldehyde for a shorter length of time and have an equivalent post-implantation level of calcification as a porcine cardiac valve leaflet contacted with a lower concentration of gluteraldehyde for a longer period of time; and in both instances, times and amounts can be adjusted so as to have less post-implantation calcification than a porcine cardiac valve leaflet contacted with 0.65% gluteraldehyde for 6 hours. Additional combinations of fixative, concentration, temperature, and time to attain a level of calcification in an isolated porcine cardiac valve tissue of 60% or less than that of a leaflet contacted with 0.65% gluteraldehyde for 6 hours, at the same post-implantation interval, can be determined by those of skill in the art using standard methods as described herein.

In some embodiments, the calcification level of the isolated porcine cardiac valve leaflet may be 60%, 50%, 40%, 30%, 20%, 15%, 10%, 5%, 2%, 1%, or less of identical-interval, post implantation calcification levels of a porcine cardiac valve leaflet contacted 6 hours with 0.65% gluteraldehyde. The percentages will be understood to represent a range, which is inclusive from 80% through 0%. Thus, the percentage can be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 percent and so on, up to 80%, embracing every integer therebetween.

In some embodiments, the contact of the porcine cardiac valve leaflet with the exogenous fixative is for a period ranging from 120 minutes to less than 0.5 minutes. In some embodiments, the exogenous fixative is gluteraldehyde. In other embodiments, the exogenous fixative may be, but is not limited to acetone or alcohol.

As will be understood by those of ordinary skill in the art, fresh versus frozen and unfixed versus minimally fixed are interrelated variables and the pathway selected may depend upon practical circumstances such as the availability of fresh material and particular patient parameters. In some instances, minimally fixed tissue (fresh or frozen) may be preferred and in other instances unfixed and particularly fresh unfixed, may be preferred.

Another aspect of the invention is the method of treating a patient by implanting an isolated porcine cardiac valve leaflet into the patient. As used herein, the patient is a human, non-human primate, horse, cow, sheep, or pig. In all embodiments human patients are preferred. Prior to implantation, the isolated porcine cardiac valve leaflet may be contacted with an exogenous fixative agent, or in other embodiments, the isolated cardiac valve leaflet is not contacted with an exogenous fixative agent. In some embodiments the isolated porcine cardiac valve leaflet has been frozen and is thawed prior to implantation and in other embodiments the isolated porcine cardiac valve leaflet was not frozen prior to implantation. Particularly important patients to which the present invention can be applied are patients in need of replacement cardiac valves.

In the invention, an isolated porcine cardiac valve leaflet kit 8 (FIG. 1) may include a package (2) containing the frozen porcine cardiac valve leaflet (not shown) which is not contacted with any exogenous fixative, contained sterile within a sealed plastic bag (4) in an extracellular solution and instructions (6) for the processing the valve leaflet for implantation in a patient. In other embodiments, the kit is an isolated porcine cardiac valve leaflet, which has been contacted with an exogenous fixative, contained sterile within a sealed plastic bag in an extracellular solution, and instructions for processing the valve leaflet for implantation in a patient. In some embodiments, 1, 2, 3 or more cardiac leaflets are packaged sterile together or in separate bags in the kit.

EXAMPLES

Methods

Experimental Animals: Heterotopic pig-to-primate cardiac xenotransplantation was performed to test the immune reaction against fresh, unmanipulated porcine valves. Olive baboons (Papio Anubis) served as transplant recipients. Wild-type or transgenic pigs expressing the human CD59/DAF or MCP complement regulatory proteins served as cardiac donors. The construction of transgenic pigs bearing human complement regulatory proteins was previously described (Chen et al, Xenotransplantation, 6:122–32. 1999). Briefly, large genomic clones encompassing the genes encoding human CD59 and DAF were microinjected into fertilized porcine oocytes to generate transgenic pigs using standard techniques (Logan et al, Meth Enzym, 435. 1994). Both clones are approximately 90 kb and contain 10 to 20 kb of the 5' and 3' flanking sequences of their respective genes. $G_1$ offspring from one founder that was transgenic for both human CD59 and DAF were used as cardiac donors. All animals received humane care in accordance with the guidelines of the Harvard University Animal Care Committee, and the "Guide for the Care and Use of Laboratory Animals" prepared by the Institute of Laboratory Animal Resources and published by the National Institutes of Health (NIH publications No. 86–23, revised 1985.)

Anesthesia. For invasive procedures and anesthesia induction, sedation was achieved using ketamine hydrochloride (10 mg/kg i.m.) in baboons and telazol (5 mg/kg i.m.) in pigs. Respiratory secretions were controlled with atropine sulfate (0.03 mg/kg). Anesthesia was maintained with inhalational isoflurane (1.3–2.0%). Intraoperatively both pigs and baboons were monitored with electrocardiography, non-invasive blood-pressure monitoring, and pulse-oximetry. All baboons received antibiotic coverage with cefazolin (20 mg/kg i.m. bid) and pain control with butrenorphine (0.005 mg/kg bid) postoperatively for 5 days. In the event of diminished fluid or caloric intake, recipients received their calculated daily needs as intravenous crystalloid solution or Ensure tube feeds.

Heterotopic Heart Transplantation: Heart transplantation was performed in the abdominal cavity as previously described (Adams et al, Annals of Thoracic Surgery, 68:265–8. 1999). Pigs were anesthetized, received systemic anticoagulation with heparin (100 IU/kg i.v.) following which the heart was harvested in a standard fashion after protection by 500 cc of antegrade cold crystalloid cardioplegic solution (dextrose 2.5%, NaCI 0.45%, potassium 30 meq/l, bicarbonate 5 meq/l). Transplant organ ischemic time varied between 45 to 55 minutes.

Immunonsupression: The transplant recipients received daily immunosuppression starting 15 days prior to transplantation. The immunosuppressive regimen consisted of cyclosporine (7 mg/kg i.m.), methylprednisolone (10 mg/kg i.m.), cyclophosphamide (10 mg/kg i.m.), and soluble carbohydrate (50 mg/kg i.v.).

Evaluation of Transplant Organ Function: An implantable telemetric system (Data Science International, St. Paul, Minn.) was used to continuously follow graft cardiac rhythm as an indicator of viability in awake recipients (Adams et al, Annals of Thoracic Surgery, 68:265–8. 1999). Grafts were explanted when the telemetric signal showed complete cessation of cardiac contractility.

Histopathologic Studies of the Porcine Valves: After graft explantation, aortic and pulmonary valves were carefully dissected and either snap-frozen in Tissue Freezing Medium (Triangle Biomedical Sciences, Durham, N.C.) and liquid nitrogen or fixed in Carnoy's solution and embedded in paraffin. Paraffin sections were sectioned at 5 μm thickness and stained with hematoxylin and eosin. Biotinylated-lectin from Grifonia simplicifolia (GSI; Sigma, St. Louis, Mo.) was used to stain α-Gal on porcine endothelium. Cryostat sections were immunostained using standard indirect immunoperoxidase avidin-biotin techniques previously summarized (Chen et al, Xenotransplantation, 6:1–6. 1999), with monoclonal antibodies specific for IgM (Biodesign International, Kennebunk, Me.) and MAC (C5–9; Dako, Carpinteria, Calif.). The signal was developed with the avidin-peroxidase system (ABC kit, Vector Lab, Burlingame, Calif.).

Example 1 Endothelium of Porcine Valves and Cardiac Microvasculature

To examine mechanisms of xenograft valve prosthetic failure, porcine xenografts in primates were examined. Porcine cardiac xenograft rejection in primates is triggered by IgM antibodies against galactose α 1,3 galactoase (α Gal) on endothelium, with ensuing membrane attach complex (MAC) deposition. Glutaraldehyde fixation may remove antigenicity, albeit at the expense of tissue viability, and fixed valves eventually undergo degenerative failure. To clarify whether fresh porcine valves in primates are subject to the same rejection mechanisms as vascularized tissues, xenotransplants from pigs to primates were performed.

To see whether α-Gal is equally expressed by the endothelium of valve leaflets and cardiac microvasculature, untransplanted porcine hearts (n=6) were examined. Cardiac microvascular endothelium had strong α-Gal expression. In comparison, neither aortic valves nor pulmonary valves had any detectable α-Gal expression.

Example 2 Porcine Valves in Hyperacute Rejection

To examine the susceptibility of wild-type pig valves to IgM-mediated hyperacute attacks, wild-type pig hearts (n=3) were transplanted into unmodified baboon recipients. The porcine xenografts were hyperacutely rejected 60 to 80 minutes after implantation. The hearts became edematous, cyanotic, and engorged. Histological examination of the rejected graft showed signs of thrombi, interstitial hemorrhage, and edema. There was extensive microvascular IgM and MAC deposition on the microvascular endothelium. Both aortic and pulmonary valves were intact and immunohistochemistry of pulmonary and aortic valves showed no signs of either IgM or MAC.

Example 3 Porcine Valves in Delayed Xenograft Rejection

To investigate the issue of whether porcine valves are immune to attacks by other primate anti-porcine antibodies and cell-mediated rejection (Platt et al, Xenotransplantation, 5:169–75. 1998), (Bach et al, Immunol Today, 17:379–84. 1996) transgenic pigs expressing human CD59/DAF proteins (n=3) were utilized as heart donors. These transgenic porcine hearts survived for 5, 7, and 11 days in baboon recipients. The xenografts became progressively edematous with weaker contractility. Xenotransplant biopsies showed some microvascular IgM deposition on the day of transplant and the intensity of staining progressively increased until rejection, correlating with increased microvascular thrombosis. There was no detectable MAC in early biopsies. MAC deposition was highly detectable in explanted xenografts. Explanted xenografts showed mild to moderate cellular infiltrate and extensive myocytic damage. Both aortic and pulmonary valves from rejected xenografts were intact. There were no signs of cellular infiltrate. The valve leaflets did not show either IgM or MAC deposition.

Except where explicitly described otherwise, terms used in the singular also are meant to embrace the plural, and vice versa. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference.

What is claimed is:

1. A method of treating a patient comprising implanting into the patient a viable isolated porcine cardiac valve leaflet that has not been contacted with an exogenous fixative.

* * * * *